United States Patent
Chen et al.

(10) Patent No.: US 12,408,880 B2
(45) Date of Patent: Sep. 9, 2025

(54) DEFLECTION ELECTRODE ASSEMBLY, X-RAY SOURCE, AND X-RAY IMAGING SYSTEM

(71) Applicants: TSINGHUA UNIVERSITY, Beijing (CN); Nuctech Company Limited, Beijing (CN); NuRay Technology Co., Ltd., Jiangsu (CN)

(72) Inventors: Zhiqiang Chen, Beijing (CN); Huaping Tang, Beijing (CN); Xin Jin, Beijing (CN)

(73) Assignees: TSINGHUA UNIVERSITY (CN); Nuctech Company Limited (CN); NuRay Technology Co., Ltd. (CN)

( * ) Notice: Subject to any disclaimer, the term of this patent is extended or adjusted under 35 U.S.C. 154(b) by 186 days.

(21) Appl. No.: 18/011,388

(22) PCT Filed: Jul. 2, 2021

(86) PCT No.: PCT/CN2021/104270
§ 371 (c)(1),
(2) Date: Dec. 19, 2022

(87) PCT Pub. No.: WO2022/028173
PCT Pub. Date: Feb. 10, 2022

(65) Prior Publication Data
US 2023/0255576 A1    Aug. 17, 2023

(30) Foreign Application Priority Data
Aug. 4, 2020  (CN) .......................... 202010772301.1

(51) Int. Cl.
*A61B 6/00* (2024.01)
*A61B 6/03* (2006.01)
*A61B 6/40* (2024.01)

(52) U.S. Cl.
CPC .................. *A61B 6/40* (2013.01); *A61B 6/03* (2013.01); *A61B 6/54* (2013.01)

(58) Field of Classification Search
CPC .. H01J 29/70; H01J 29/74; H01J 29/76; H01J 29/46; H01J 29/465; H01J 29/02;
(Continued)

(56) References Cited

U.S. PATENT DOCUMENTS

| | | | |
|---|---|---|---|
| 4,926,452 A | 5/1990 | Baker et al. | |
| 4,955,681 A | 9/1990 | Sekihara et al. | |

(Continued)

FOREIGN PATENT DOCUMENTS

| | | |
|---|---|---|
| CN | 102543635 A | 7/2012 |
| CN | 102652346 A | 8/2012 |

(Continued)

OTHER PUBLICATIONS

CNIPA; Second Office Action for Chinese Patent Application No. 202010772301.1 dated Jan. 10, 2023, 7 pages.

(Continued)

*Primary Examiner* — Don K Wong
(74) *Attorney, Agent, or Firm* — K&L Gates LLP

(57) ABSTRACT

The present application relates to a deflection electrode assembly, an X-ray source, and an X-ray imaging system. The deflection electrode assembly includes: a first electrode plate, including a first connection portion and a plurality of first tooth portions, wherein the first electrode plate is formed as a comb shape; and a second electrode plate, including a second connection portion and a plurality of second tooth portions, wherein the second electrode plate is formed as a comb shape. The first electrode plate and the second electrode plate are not in contact with each other, and the plurality of first tooth portions and the plurality of second tooth portions are arranged at least partially in a staggered (Continued)

manner to form a plurality of electron beam passageways; each electron beam passageway is located between adjacent first and second tooth portions.

18 Claims, 5 Drawing Sheets

(58) Field of Classification Search
CPC .. H01J 29/08; H01J 29/48; H01J 29/80; H01J 29/467; H01J 35/00; H01J 35/04; H01J 35/045; H01J 35/112; H01J 37/04; H01J 37/147

See application file for complete search history.

(56) References Cited

U.S. PATENT DOCUMENTS

| | | | |
|---|---|---|---|
| 4,980,613 A * | 12/1990 | Miyama | H04N 9/12 315/366 |
| 5,189,335 A | 2/1993 | Sekihara et al. | |
| 5,446,337 A | 8/1995 | Yokomakura et al. | |
| 6,980,627 B2 | 12/2005 | Qiu et al. | |
| 2020/0170097 A1 | 5/2020 | Tan et al. | |

FOREIGN PATENT DOCUMENTS

| | | | | |
|---|---|---|---|---|
| CN | 104465279 B | 8/2017 | | |
| CN | 104470177 B | 8/2017 | | |
| CN | 107464734 A | 12/2017 | | |
| EP | 0459496 A2 * | 12/1991 | | H01J 31/12 |
| EP | 0316871 A2 | 5/1998 | | |
| JP | 2008262789 A | 10/2008 | | |

OTHER PUBLICATIONS

JPO; Decision to Grant for Japanese Patent Application No. 2022-576850 dated Nov. 27, 2023, 5 pages.

IP Australia; Second Examination Report for Australian Patent Application No. 2021323079 dated Dec. 19, 2023, 3 pages.

IP Australia; First Examination Report for Australian Patent Application No. 2021323079 dated Sep. 21, 2023, 2 pages.

International Search Report and Written Opinion issued on Sep. 23, 2021 for International PCT application No. PCT/CN2021/104270.

First Office Action dated Jul. 4, 2022 issued for Chinese Patent Application No. 202010772301.1.

* cited by examiner

DEFLECTION ELECTRODE ASSEMBLY, X-RAY SOURCE, AND X-RAY IMAGING SYSTEM

CROSS REFERENCES TO RELATED APPLICATIONS

The present disclosure is a national phase of PCT Application No. PCT/CN2021/104270, which is filed on Jul. 2, 2021 and claims the priority to the Chinese patent application No. 202010772301.1, filed on Aug. 4, 2020 and titled by "Deflection electrode assembly, X-ray source and X-ray imaging system", both of which are incorporated here by reference in their entireties.

TECHNICAL FIELD

The present disclosure relates to a technical field of X-ray technology, in particular to a deflection electrode assembly for an X-ray source, an X-ray source and an X-ray imaging system.

BACKGROUND

X-rays are widely used in industrial non-destructive testing, security inspection, medical diagnosis and treatment. The device that generates X-rays is called an X-ray source. The X-ray source usually consists of an X-ray tube, a power supply and control system, cooling, shielding and other auxiliary devices, and the core is the X-ray tube. The X-ray tube usually consists of a cathode, an anode and a shell. The cathode generates an electron beam. The electron beam is accelerated by a high voltage electric field between the cathode and anode and impacts the anode, thus generating the X-rays. The traditional X-ray tube only has one cathode to generate electron emission, and can only produce one X-ray focus spot with a stationary position.

The new distributed X-ray source (or multi-focal X-ray source) is a kind of X-ray source with multiple cathodes and multiple targets, in which X-rays can be generated from multiple different positions. It has very significant advantages in the CT field of multi view imaging and 3D imaging. In order to generate X-rays from different positions, many patent documents have disclosed different technical solutions. For example, US patent application U.S. Pat. No. 4,926,452A deflects the electron beams through electromagnetic field scanning to generate focus spots with different positions. Since it is a continuous process that the traditional hot cathode emits electrons in cooperation with the electromagnetic field scanning, the change of position of focus spot is a continuous dynamic change and motion artifacts are generated in the X-ray imaging, and thus this solution has not been widely used. The emerging technical solution uses multiple electron sources (cathodes) to generate electron beams from different positions and generate X-rays at different positions, eliminating artifacts caused by the continuous changes of target positions, and for example, the Chinese patent CN104470177B uses multiple hot cathodes to generate electron beams from different positions, and the American patent U.S. Pat. No. 6,980,627B2 uses a field emission cold cathode to generate electron beams from different positions.

SUMMARY

With the development of X-ray 3D imaging technology, the image resolution is required to be higher and higher. The methods to obtain high-definition images usually include: continuously reducing the pixels of detector, continuously reducing the size of the focus spot, and increasing the focus spot distribution density. The physical difficulty of the first two items is getting higher and higher, and thus it becomes an important improvement direction to increase the focus spot distribution density. The hot cathode distributed light source represented by Chinese patent CN104465279B is limited by the physical size and thermal insulation requirements of the cathode itself, and thus has a large cathode spacing (usually not less than 20 mm) and a small focus spot density. The Chinese patent application CN107464734A proposes a method to increase the number of focus spots by adding deflection electrodes. However, the overall structure of this solution is relatively complicate and include compensation electrodes; the arrangement and connection of focusing electrodes are complicate, where the focusing electrodes are divided into two categories, each of which includes a large number of independent electrodes, and when installing and fixing each category of focusing electrodes, the overall installation accuracy needs to be considered, as well as the electrical insulation between each independent electrode and the installation structure, and thus the overall solution is complicate with a high cost.

Therefore, a deflection electrode assembly with simplified structure and low cost is required.

An object of the present disclosure is to provide a deflection electrode assembly, an X-ray source and an X-ray imaging system with simplified structure and reduced number of components. A further object of the present disclosure is to provide a deflection electrode assembly, an X-ray source and an X-ray imaging system that increase the number of X-ray emission positions. A further object of the present disclosure is to provide a deflection electrode assembly, an X-ray source and an X-ray imaging system that improve the imaging quality.

One aspect of the present disclosure provides a deflection electrode assembly for an X-ray source, the deflection electrode assembly includes: a first electrode plate, including a first connecting portion and a plurality of first tooth portions, the plurality of first tooth portions being disposed on the first connecting portion and spaced apart from each other, and each first tooth portion extending from the first connecting portion so that the first electrode plate is formed into a comb shape; and a second electrode plate, including a second connecting portion and a plurality of second tooth portions, the plurality of second tooth portions being disposed on the second connecting portion and spaced apart from each other, and each second tooth portion extending from the second connecting portion so that the second electrode plate is formed into a comb shape, wherein the first electrode plate and the second electrode plate are arranged such that the first electrode plate and the second electrode plate do not contact each other, and that the plurality of first tooth portions and the plurality of second tooth portions are at least partially staggered to form a plurality of electron beam passageways, each electron beam passageway is located between adjacent first tooth portion and second tooth portion.

In an existing distributed X-ray source, each electron beam passageway requires two independent electrodes to generate the deflection effect, and the number of the independent electrodes is twice that of the electron beam passageways. Therefore, the number of components is large, and the installation, fixing and electrical connection of the electrodes are complicate. In the deflection electrode assembly according to the embodiments of the present disclosure, the tooth portions of the two electrode plates are staggered, and the connecting portion of the electrode plate serves as a common connecting portion of the plurality of tooth portions, which provides structural connection for the plurality of tooth portions on the one hand, and achieves electrical connection of the plurality of tooth portions on the other hand. Therefore, each electrode plate includes the connecting portion and the plurality of tooth portions connected with each other, which greatly simplifies the installation, fixing and electrical connection of the deflection electrode assembly, and can achieve higher positioning accuracy more easily. Further, in order to achieve the deflection of the electron beam, each tooth portion (the electrode plate) needs to be applied with the same or different potential, and thus the tooth portion needs to be electrically insulated from the adjacent components (such as other opposite tooth portions, the cathode, the anode, and even structural parts that provide support). In the existing technical solution, the respective electrodes are independent of each other, and it is difficult to install the electrodes to achieve the relative insulating installation and positioning of the respective electrodes. According to the embodiments of the present disclosure, through the innovative comb structure, a plurality of electrodes with one potential are designed as one integrity (the first electrode plate) and a plurality of electrodes with another potential are designed as another integrity (the second electrode plate), the installation, fixing and electrical connection of the electrodes are greatly simplified.

According to the embodiments of the present disclosure, the first electrode plate and the second electrode plate are arranged such that one second tooth portion is disposed between every two first tooth portions, and one first tooth portion is disposed between every two second tooth portions. By staggering the tooth portions of the two electrode plates, the number of electron beam passageways can be increased, which is conducive to generating more X-ray focus spots based on fewer cathode units, thus obtaining more X-ray imaging information, reducing the cost of the distributed X-ray source and improving the image quality of the X-ray imaging system.

According to the embodiments of the present disclosure, at each electron beam passageway, opposite side surfaces of adjacent first tooth portion and second tooth portion are parallel to each other. Therefore, the deflection electric field between the two tooth portions is relatively uniform, which is conducive to controlling the deflection of the electron beam and the deviation of the focus spot position.

According to the embodiments of the present disclosure, the plurality of first tooth portions are spaced at the same spacing on the first connecting portion, the plurality of second tooth portions are spaced at the same spacing on the second connecting portion, and the plurality of electron beam passageways are distributed at the same spacing. Therefore, the respective tooth portions are distributed uniformly and equally spaced, and the respective electron beam passageways are also distributed uniformly and equally spaced. This is conducive to simplifying the processing of the electrode plates and the installation of the deflection electrode assembly, and meanwhile can make the deflection and focusing effects of the electron beams more uniform.

According to the embodiments of the present disclosure, the plurality of first tooth portions have the same shape, and the plurality of second tooth portions have the same shape.

According to the embodiments of the present disclosure, the first connecting portion includes a first inner surface arranged with the plurality of first tooth portions, and the second connecting portion includes a second inner surface arranged with the plurality of second tooth portions, the first inner surface is perpendicular to the side surfaces of the first tooth portions, and the second inner surface is perpendicular to the side surfaces of the second tooth portions. Therefore, the electrode plate can have a more regular structure, which is convenient for processing and installation.

According to the embodiments of the present disclosure, each electron beam passageway includes an input side of electron beam and an output side of electron beam; each first tooth portion of the first electrode plate includes an upper surface on the output side of the electron beam and a lower surface on the input side of the electron beam, and the upper surfaces of the plurality of first tooth portions are all located in the same plane; each second tooth portion of the second electrode plate includes an upper surface on the output side of the electron beam and a lower surface on the input side of the electron beam, and the upper surfaces of the plurality of second tooth portions are all located in the same plane.

According to the embodiments of the present disclosure, the first electrode plate and the second electrode plate are arranged such that the upper surfaces of the plurality of first tooth portions and the upper surfaces of the plurality of second tooth portions are located in the same plane. The upper surfaces of the two electrode plates are located in the same plane, which is conducive to simplifying the processing and installation of the electrode plates. In addition, when the deflection electrode assembly is installed in the X-ray source, it is beneficial for the upper surfaces of the electrode plates to be arranged parallel to the opposite surface of the anode, so that a more uniform electric field can be formed between the electrode plates and the anode, and thus the electron beams from the respective electron beam passageways can have a more consistent focusing and accelerating effect.

According to the embodiments of the present disclosure, the first electrode plate and the second electrode plate are arranged such that the lower surfaces of the plurality of first tooth portions and the lower surfaces of the plurality of second tooth portions are all located in the same plane. The lower surfaces of the electrode plates are also located in the same plane, which is conducive to simplifying the processing and installation of the electrode plates, and at the same time, when the deflection electrode assembly is installed in the X-ray source, it is conducive to the installation of the cathode units.

According to the embodiments of the present disclosure, the first tooth portion and the second tooth portion both have a rectangular shape.

According to the embodiments of the present disclosure, the first tooth portion includes an end surface away from the first connecting portion, and the second tooth portion includes an end surface away from the second connecting portion; and the first electrode plate and the second electrode plate are arranged such that a distance between the end surface of the first tooth portion and the second inner surface of the second connecting portion is in a range from 0.1 mm to 10 mm, and a distance between the end surface of the second tooth portion and the first inner surface of the first connecting portion is in a range from 0.1 mm to 10 mm. With the above insulation distance, it can achieve insulation for tens of volts to thousands of volts between the two electrode plates.

According to the embodiments of the present disclosure, the first electrode plate and the second electrode plate are arranged such that the distance between the end surface of the first tooth portion and the second inner surface of the second connecting portion is in a range from 0.5 mm to 5 mm, and the distance between the end surface of the second tooth portion and the first inner surface of the first connecting portion is in a range from 0.5 mm to 5 mm. With the above insulation distance, it is conducive to meeting the requirements of processing accuracy and installation accuracy.

According to the embodiments of the present disclosure, the first electrode plate and the second electrode plate are arranged such that each electron beam passageway has a length between 3 mm and 50 mm from the input side of the electron beam to the output side of the electron beam. If the electron beam passageway is too short, the deflection potential will be too high, which will increase the cost of the potential controller. If the electron beam passageway is too long, the deflection electrode assembly occupies a large space in the X-ray source, which is not conducive to reducing the size and weight of the X-ray source.

According to the embodiments of the present disclosure, the deflection electrode assembly further includes a potential controller which is electrically connected to the first electrode plate and the second electrode plate respectively, wherein the potential controller can supply electric power to the first electrode plate and the second electrode plate to generate a plurality of potential differences between the first electrode plate and the second electrode plate.

Another aspect of the present application provides an X-ray source, including: a plurality of cathode units, for generating electron beams from different positions; an anode, for receiving the electron beams from different positions; and the deflection electrode assembly according to the embodiments of the present disclosure, the first electrode plate and the second electrode plate of the deflection electrode assembly being arranged between the plurality of cathode units and the anode, wherein each cathode unit is arranged to align one electron beam passageway of the deflection electrode assembly, so that the electron beams generated by the plurality of cathode units can pass through the corresponding electron beam passageways respectively and reach the anode.

In the X-ray source according to the embodiments of the present disclosure, when the two electrode plates of the deflection electrode assembly are applied with different potentials, the electron beam will deflect. Further, when a high voltage is applied to the anode, a focusing electric field can be generated at the outlet of the electron beam passageway of the deflection electrode assembly to focus the electron beam. Therefore, during movement of the electron beam, the focusing and deflection are achieved by two electric fields respectively, while the final effect is superposed, that is, when passing through the deflection electrode assembly according to the embodiments of the present disclosure, the electron beam is focused and deflected at the same time.

According to the embodiments of the present disclosure, the X-ray source further includes a cathode controller, which is electrically connected to the plurality of cathode units respectively to control each cathode unit to generate or not to generate the electron beam.

According to the embodiments of the present disclosure, the X-ray source further includes a cooperative controller, which is connected with the cathode controller and the potential controller of the deflection electrode assembly in communication, so as to send an X-ray emission request to the cathode controller and the deflection electrode assembly or receive X-ray emission information from the cathode controller and the deflection electrode assembly.

According to the embodiments of the present disclosure, wherein n kinds of potential differences between the first electrode plate and the second electrode plate of the deflection electrode assembly are provided, n≥2, and the X-ray source includes either of the following operating states: the plurality of cathode units sequentially emit electron beams for n times, and for the n times of electron beam emission of each cathode unit, the deflection electrode assembly is respectively at the n kinds of potential differences; and the plurality of cathode units performs n cycles of electron beam emission, and in the first cycle, the plurality of cathode units successively emit the electron beam once while the deflection electrode assembly remains at a first potential difference, until in the nth cycle, the plurality of cathode units successively emit the electron beam once while the deflection electrode assembly remains at the nth potential difference.

According to the embodiments of the present disclosure, the upper surfaces of the plurality of first tooth portions of the first electrode plate are located in the same plane as the upper surfaces of the plurality of second tooth portions of the second electrode plate, and are parallel to a surface of the anode facing the first electrode plate and the second electrode plate.

A further aspect of the present disclosure provides an X-ray imaging system, including: the X-ray source according to the embodiments of the present disclosure for generating X-ray from different positions.

According to the embodiments of the present disclosure, the X-ray imaging system further includes an imaging control device for acquiring X-ray emission information from the X-ray source.

DETAILED DESCRIPTION

Figure 1:
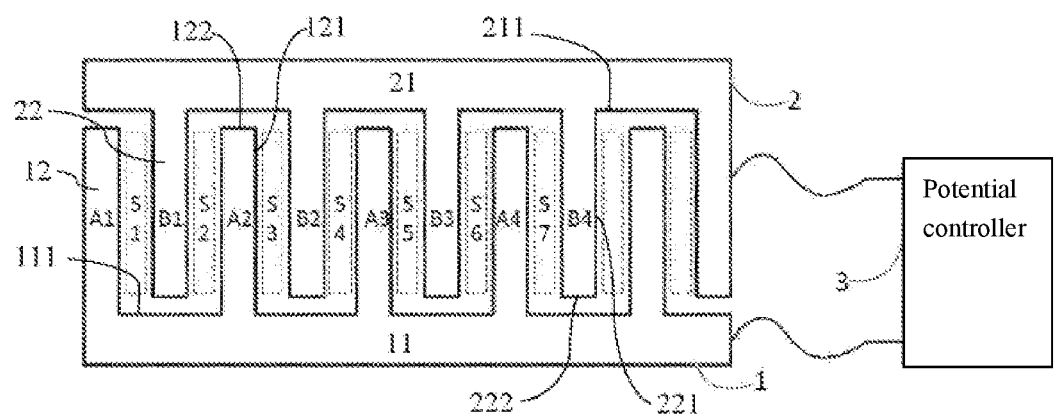
FIG. 1 is a schematic diagram of a deflection electrode assembly according to an embodiment of the present disclosure.

Hereinafter, embodiments of the present disclosure are described with reference to the accompanying drawings. The following detailed description and accompanying drawings are used to illustrate the principle of the present disclosure by example. The present disclosure is not limited to the preferred embodiments as described, and the scope of the present disclosure is defined by the claims. The present disclosure is now described in detail with reference to exemplary embodiments, some of which are illustrated in the accompanying drawings. The following description is made with reference to the accompanying drawings, and unless otherwise indicated, the same reference numerals in different drawings represent the same or similar elements. The solutions described in the following exemplary embodiments do not represent all the solutions of the present disclosure. On the contrary, these solutions are only examples of systems and methods of various aspects of the present disclosure involved in the appended claims.

Figure 2:
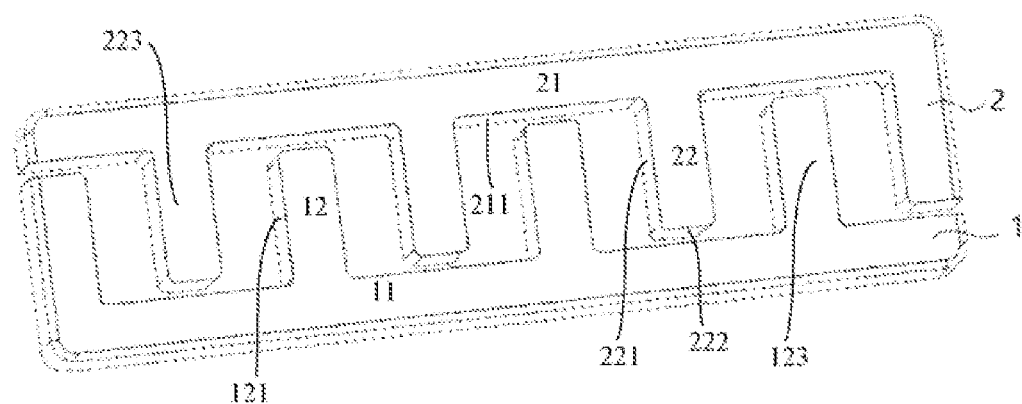
FIG. 2 is a three-dimensional schematic diagram of a deflection electrode assembly according to an embodiment of the present disclosure.

Below, the deflection electrode assembly according to the embodiments of the present disclosure is described with reference to FIG. 1 and FIG. 2. FIG. 1 is a schematic diagram of a deflection electrode assembly according to an embodiment of the present disclosure. FIG. 2 is a three-dimensional schematic diagram of a deflection electrode assembly according to an embodiment of the present disclosure.

As shown in FIG. 1 and FIG. 2, the deflection electrode assembly according to the embodiment of the present disclosure includes two electrode plates 1 and 2. In an exemplary embodiment, the electrode plate 1 and the electrode plate 2 have the same structure. In some embodiments, the electrode plate 1 and the electrode plate 2 may have different structures.

The electrode plate 1 includes a connecting portion 11 and a plurality of tooth portions 12. The plurality of tooth portions 12 are disposed on the connecting portion 11 and spaced apart from each other. In an exemplary embodiment, the plurality of tooth portions 12 are spaced at the same spacing. The connecting portion 11 serves as a common connecting portion, and provides structural support for the plurality of tooth portions 12. The electrode plate 1 is formed into a comb shape, where the plurality of tooth portions 12 extend out from the connecting portion 11.

The electrode plate 2 includes a connecting portion 21 and a plurality of tooth portions 22. The plurality of tooth portions 22 are disposed on the connecting portion 21 and spaced apart from each other. In an exemplary embodiment, the plurality of tooth portions 22 are spaced at the same spacing. The connecting portion 21 serves as a common connecting portion, and provides structural support for the plurality of tooth portions 22. The electrode plate 2 is formed into a comb shape, where the plurality of tooth portions 22 extend out from the connecting portion 21.

As shown in FIG. 1 and FIG. 2, the electrode plate 1 and the electrode plate 2 are arranged not to contact each other, and the plurality of tooth portions 12 and the plurality of tooth portions 22 are staggered to form a plurality of electron beam passageways. Each electron beam passageway is located between adjacent tooth portion 12 and tooth portion 22. The electron beam emitted from a cathode can pass through the electron beam passageway and then impact an anode (described in detail below). In an exemplary embodiment, one tooth portion 22 is disposed between every two tooth portions 12, and one tooth portion 12 is disposed between every two tooth portions 22, as shown in FIG. 1 and FIG. 2. For example, if the plurality of tooth portions 12 of electrode plate 1 are respectively named A1, A2, A3, A4, . . . , the plurality of tooth portions 22 of electrode plate 2 are respectively named B1, B2, B3, B4, . . . , and the plurality of electron beam passageways are respectively named S1, S2, S3, S4, . . . , then the tooth portions 12, 22 of the electrode plates 1, 2 and the electron beam passageways are arranged in the following order: A1, S1, B1, S2, A2, S3, B2, S4, A3, S5, B3, S6, A4, S7, B4, . . . , as shown in FIG. 1.

According to the embodiments of the present disclosure, the deflection electrode assembly can include a potential controller 3. The potential controller 3 is electrically connected to the electrode plate 1 and the electrode plate 2 respectively so as to supply electric power to the electrode plate 1 and the electrode plate 2 respectively. The potential controller 3 can provide potential $V_A$ to the electrode plate 1 and potential $V_B$ to the electrode plate 2. The potential $V_A$ and potential $V_B$ can be the same or different, for example, may be zero potential, positive potential or negative potential respectively. The potential controller 3 can control the potential difference ($V_A$-$V_B$) between the electrode plate 1 and the electrode plate 2, so that a plurality of potential differences is provided between the electrode plate 1 and the electrode plate 2. When the potential difference between the electrode plate 1 and the electrode plate 2 is different, the electron beam passageway between the adjacent tooth portion 12 and tooth portion 22 can be in a different electric field. In an exemplary embodiment, the potential difference between the electrode plate 1 and the electrode plate 2 may have the following three states: the potential difference is zero (i.e. $V_A$=$V_B$); the potential difference is positive (i.e. $V_A$>$V_B$, for example, $V_A$-$V_B$=+100V); or the potential difference is negative (i.e. $V_A$<$V_B$, for example, $V_A$-$V_B$=-100V).

According to some embodiments of the present disclosure, as shown in FIG. 1, the connecting portion 11 of the electrode plate 1 includes an internal surface 111, and the plurality of tooth portions 12 are arranged on the internal surface 111 of the connecting portion 11, that is, the tooth portions 12 extend out from the internal surface 111 of the connecting portion 11. In an exemplary embodiment, the inner surface 111 is formed as a flat plane. In an exemplary embodiment, the plurality of tooth portions 12 of the electrode plate 1 are uniformly distributed on the connecting portion 11 at the same spacing. According to some embodiments of the present disclosure, as shown in FIG. 1 and FIG. 2, the connecting portion 21 of the electrode plate 2 includes an inner surface 211, and the plurality of tooth portions 22 are arranged on the inner surface 211 of the connecting portion 21, that is, the tooth portions 22 extend out from the inner surface 211 of the connecting portion 21. In an exemplary embodiment, the inner surface 211 is formed as a flat plane. In an exemplary embodiment, the plurality of tooth portions 22 of the electrode plate 2 are uniformly distributed on the connecting portion 21 at the same spacing.

According to some embodiments of the present disclosure, the electrode plate 1 and the electrode plate 2 are arranged such that the plurality of electron beam passageways are distributed at the same spacing. In an exemplary embodiment, the plurality of electron beam passageways have the same size.

According to some embodiments of the present disclosure, as shown in FIG. 1 and FIG. 2, the tooth portion 12 includes a side surface 121 and an end surface 122. One end of the tooth portion 12 is connected to the connecting portion 11 (the inner surface 111) and the other end has the end surface 122. In an exemplary embodiment, the inner surface 111 of the connecting portion 11 is perpendicular to the side surface 121 of the tooth portion 12. According to some embodiments of the present disclosure, as shown in FIG. 2, the tooth portion 22 includes a side surface 221 and an end surface 222. One end of the tooth portion 22 is connected to the connecting portion 21 (the inner surface 211), and the other end has the end surface 222. In an exemplary embodiment, the inner surface 211 of the connecting portion 21 is perpendicular to the side surface 221 of the tooth portion 22.

In an exemplary embodiment, the opposite side surfaces 121 and 221 of the adjacent tooth portion 12 and tooth portion 22 are parallel to each other, that is, the side surfaces 121 and 221 opposite each other and forming the electron beam passageway are parallel.

In an exemplary embodiment, the plurality of tooth portions 12 of the electrode plate 1 have the same shape, for example, are each roughly rectangular, as shown in FIG. 1 and FIG. 2. In an exemplary embodiment, the plurality of tooth portions 22 of the electrode plate 2 have the same shape, for example, are each roughly rectangular, as shown in FIG. 1 and FIG. 2. In some embodiments, the connecting portions 11 and 21 are each roughly rectangular in shape, respectively.

The electrode plate 1 and the electrode plate 2 are arranged not to contact each other so as to maintain a certain insulation distance. According to some embodiments of the present disclosure, the shortest distance between the electrode plate 1 and the electrode plate 2 is located between the inner surface 111 of the connecting portion 11 and the end surface 222 of the tooth portion 22, and/or between the inner surface 211 of the connecting portion 21 and the end surface 122 of the tooth portion 12. In an exemplary embodiment, the electrode plate 1 and the electrode plate 2 are arranged such that the inner surface 111 of the connecting portion 11 is parallel to the end surface 222 of the tooth portion 22 and/or the inner surface 211 of the connecting portion 21 is parallel to the end surface 122 of the tooth portion 12. In an exemplary embodiment, the distance between the end surface 122 of the tooth portion 12 and the inner surface 211 of the connecting portion 21 is in a range from 0.1 mm to 10 mm, for example, from 0.5 mm to 5 mm; and/or the distance between the end surface 222 of the tooth portion 222 and the inner surface 111 of the connecting portion 11 is in a range from 0.1 mm to 10 mm, for example, from 0.5 mm to 5 mm.

According to some embodiments of the present disclosure, as shown in FIG. 2, the tooth portion 12 includes an upper surface 123 and a lower surface (not shown). In an exemplary embodiment, the upper surface 123 and the lower surface of the tooth portion 12 are perpendicular to the inner surface 111 of the connecting portion 11 and the side surface 121 of the tooth portion 12, that is, the upper surface 123 and the lower surface are distributed along a thickness direction of the tooth portion. In an exemplary embodiment, the upper surfaces 123 of the plurality of tooth portions 12 are all located in the same plane. In some embodiments, the lower surfaces of the plurality of tooth portions 12 are also located in the same plane. In this paper, the upper surface is a surface on an output side of the electron beam, that is, a surface facing the anode (see below); the lower surface is a surface on an input side of the electron beam, that is, a surface facing the cathode unit (see below); and the thickness direction is a direction from the input side of the electrode beam to the output side of the electron beam.

According to some embodiments of the present disclosure, as shown in FIG. 2, the tooth portion 22 includes an upper surface 223 and a lower surface (not shown). In an exemplary embodiment, the upper surface 223 and the lower surface of the tooth portion 22 are perpendicular to both the inner surface 211 of the connecting portion 21 and the side surface 221 of the tooth portion 22, that is, the upper surface 223 and the lower surface are distributed along a thickness direction of the tooth portion. In an exemplary embodiment, the upper surfaces 223 of the plurality of tooth portions 22 are all located in the same plane. In some embodiments, the lower surfaces of the plurality of tooth portions 22 are also located in the same plane.

In an exemplary embodiment, the electrode plate 1 and the electrode plate 2 are arranged such that the upper surfaces 123 of the plurality of tooth portions 12 and the upper surfaces 223 of the plurality of tooth portions 22 are all located in the same plane. In some embodiments, the entire upper surface of the electrode plate 1 and the entire upper surface of the electrode plate 2 are both located in the same plane. In an exemplary embodiment, the electrode plate 1 and the electrode plate 2 are arranged such that the lower surfaces of the plurality of tooth portions 12 and the lower surfaces of the plurality of tooth portions 22 are all located in the same plane. In some embodiments, the entire lower surface of the electrode plate 1 and the entire lower surface of the electrode plate 2 are both located in the same plane.

According to some embodiments of the present disclosure, the electrode plate 1 and the electrode plate 2 are arranged such that the electron beam passageway has a length from the input side of the electron beam to the output side of the electron beam (the size in the thickness direction), between 3 mm and 50 mm.

Figure 3:
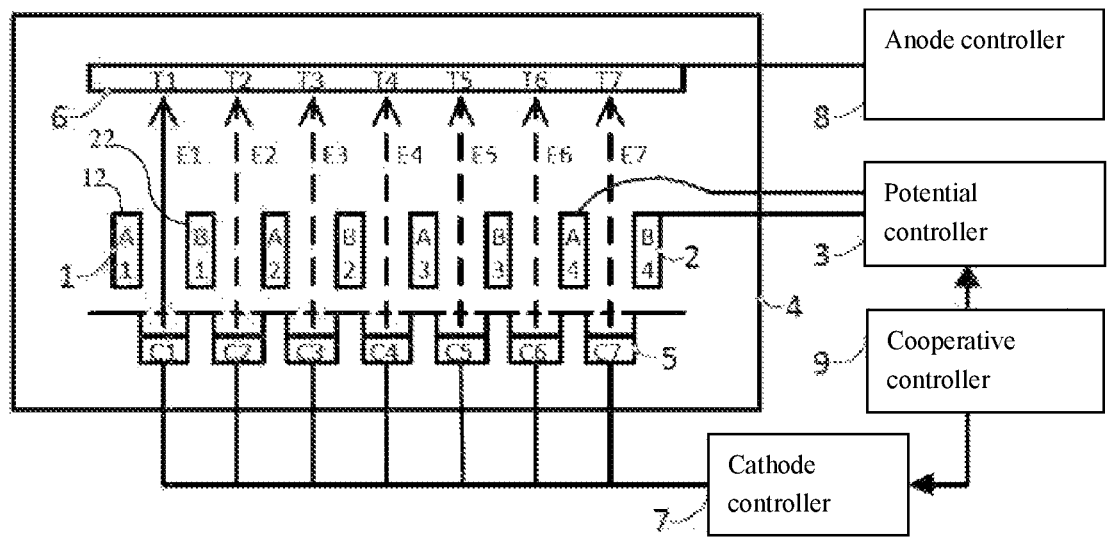
FIG. 3 is a structural diagram of an X-ray source according to an embodiment of the present disclosure.

Next, an X-ray source according to the embodiments of the present disclosure will be described with reference to FIG. 3. FIG. 3 is a structural schematic diagram of an X-ray source according to an embodiment of the present disclosure.

As shown in FIG. 3, the X-ray source according to the embodiments of the present disclosure includes a chamber 4, a deflection electrode assembly as described above, a plurality of cathode units 5, and an anode 6. FIG. 3 shows the chamber 4, the electrode plate 1 and electrode plate 2 of the deflection electrode assembly, the cathode units 5 and the anode 6 in a sectioning manner.

The description of the deflection electrode assembly according to the embodiments of the present disclosure please refer to above, and will not be repeated here. FIG. 3 shows the plurality of tooth portions of electrode plates 1 and 2 and electron beam passageways between adjacent tooth portions in a sectioning manner. It should be noted that in order to facilitate explanation and prevent blurring of key points, the connecting portions of the electrode plates 1 and 2 are not shown in FIG. 3. In FIG. 3, the plurality of tooth portions of the electrode plate 1 are named A1, A2, A3, A4, . . . , the plurality of tooth portions of the electrode plate 2 are named B1, B2, B3, B4, . . . , and the tooth portions of the electrode plates 1 and 2 are arranged in the following order: A1, B1, A2, B2, A3, B3, A4, B4, . . . .

The electrode plates 1 and 2 of the deflection electrode assembly, the cathode units 5 and the anode 6 are arranged in the chamber 4. The chamber 4 is a vacuum chamber, which provides a vacuum working environment for internal components. In some embodiments, the electrode plates 1 and 2 of the deflection electrode assembly are respectively connected in the chamber 4 through insulating parts (such as ceramic insulating parts).

The plurality of cathode units 5 are used to generate electron beams from different positions. In FIG. 3, these cathode units 5 are named C1, C2, C3, C4 . . . , respectively, and these electron beams are named E1, E2, E3, E4 . . . , respectively. The anode 6 is used to receive the electron beams from different positions and thus generate X-rays. In FIG. 3, the focus spot positions (electron beam receiving positions) on the anode 6 are named T1, T2, T3, T4 . . . , respectively. In an exemplary embodiment, the upper surfaces of the plurality of tooth portions of the electrode plate 1 and the upper surfaces of the plurality of tooth portions of the electrode plate 2 are all located in the same plane, and the upper surfaces of the tooth portions of the electrode plates 1 and 2 lie in a plane parallel to the surface of the anode 6 (the electron beam receiving surface of the anode 6) facing the electrode plates 1 and 2. In an exemplary embodiment, the lower surfaces of the plurality of tooth portions of the electrode plate 1 and the plurality of tooth portions of the electrode plate 2 are all located in the same plane, and the lower surfaces of the tooth portions of the electrode plates 1 and 2 lie in a plane parallel to the surfaces of the plurality of cathode units 5 (the electron beam emission surfaces of the cathode units 5) facing the electrode plates 1 and 2.

The electrode plates 1 and 2 of the deflection electrode assembly are arranged between the plurality of cathode units 5 and the anode 6, and the cathode units 5 (the emission positions of the electron beams of the cathode units 5) are respectively aligned with the corresponding electron beam passageways of the deflection electrode assembly. Thus, the electron beams generated from the cathode units 5 can pass through the corresponding electron beam passageways of the deflection electrode assembly, and impact the anode 6 after being deflected and/or focused by the deflection electrode assembly (as described in detail below). Each electron beam passageway includes the input side of the electron beam and the output side of the electron beam. In this paper, the input side of the electron beam is the side facing the cathode units 5, and the output side of the electron beam is the side facing the anode 6.

According to some embodiments of the present disclosure, the X-ray source may further include a cathode controller 7 and an anode controller 8. In some embodiments, the cathode controller 7, the anode controller 8, and/or a cooperative controller 9 may be disposed outside the chamber 4. The potential controller 3 of the deflection electrode assembly can also be disposed outside the chamber 4. The cathode controller 7 is electrically connected with the plurality of cathode units 5 respectively. The anode controller 8 is electrically connected with the anode 6. For example, the electrical connection lines of the cathode controller 7, the anode controller 8 and the potential controller 3 can be electrically connected to the plurality of cathode units 5, the anode 6, and electrode plates 1 and 2 of the deflection electrode assembly through connectors (such as ceramic insulated connectors) penetrating the chamber 4.

The cathode controller 7 is used to control the working state of each cathode unit 5, that is, to generate or not to generate electron beam. The anode controller 8 is used to apply a high voltage to the anode 6, usually a high voltage of tens to hundreds of kilovolts. Therefore, by applying the high voltage to the anode 6, an accelerating electric field is generated between the anode 6 and the cathode unit 5, so that the electron beam generated from the cathode unit 5 is accelerated and impacts the anode 6, thereby generating X-rays. Further, by applying the high voltage to the anode 6, a focusing electric field can also be generated at the outlet position (the output side of the electron beam) of the electron beam passageway of the deflection electrode assembly, so as to focus the electron beam (as described in detail below).

In some embodiments, the X-ray source may further include a cooperative controller 9. The cooperative controller 9 can be connected with the potential controller 3 and the cathode controller 7 in communication, for example, through wired communication or wireless communication, to perform cooperative control to the potential controller 3 and the cathode controller 7. In an exemplary embodiment, the cooperative controller 9 can send an X-ray emission request to the cathode controller 7 and the potential controller 3 or receive X-ray emission information from the cathode controller 7 and the potential controller 3. The cooperative controller 9 may send instructions to the cathode controller 7, such as instructions on the electron beam emission state of the cathode unit 5, and/or obtain information from the cathode controller 7, such as information on the electron beam emission state of the cathode unit 5. Further, the cooperative controller 9 can send instructions to the potential controller 3, such as instructions on the potential difference state between the electrode plate 1 and electrode plate 2, and/or obtain information from the potential controller 3, such as information on the potential difference state between the electrode plate 1 and electrode plate 2. For example, when the cathode controller 7 controls a certain cathode unit to generate or not generate electron beam, the cooperative controller 9 can notify the potential controller 3 of applying what potential to the electrode plates 1 and 2 of the deflection electrode assembly so as to generate the required potential difference. The cooperative controller 9 can control the X-ray focus spot position of the X-ray source in real time by communicating with the cathode controller 7 and the potential controller 3, or feedback the X-ray focus spot position to other control devices in real time.

Figure 4:
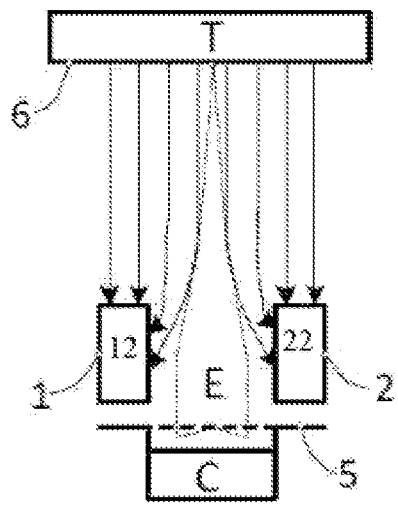
FIG. 4 is a schematic diagram of a focusing state of a deflection electrode assembly according to an embodiment of the present disclosure.
Figures 5A, 5B, 5C:
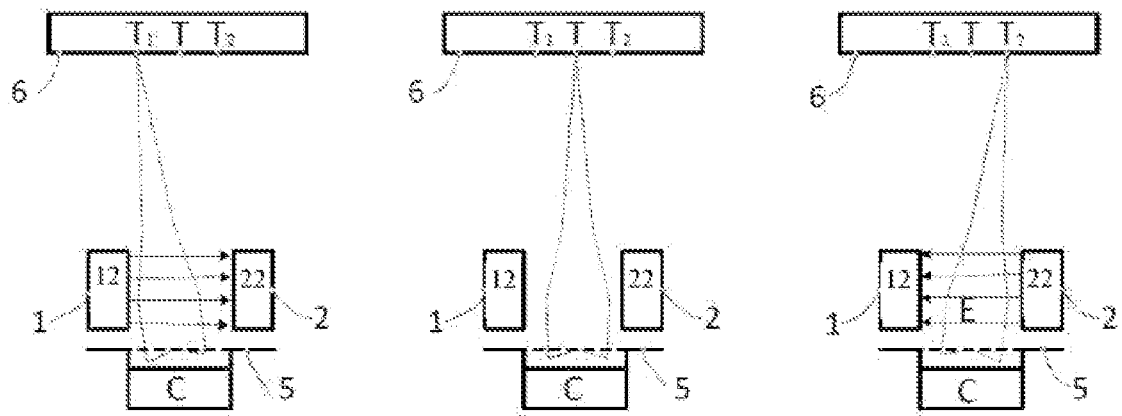
FIGS. 5a to 5c are schematic diagrams of a deflection state of a deflection electrode assembly according to an embodiment of the present disclosure.

The operating principle of the deflection electrode assembly according to the embodiments of the present disclosure is described below with reference to FIG. 3, FIG. 4 and FIG. 5a to 5c. FIG. 4 is a schematic diagram of a focusing state of a deflection electrode assembly according to the embodiments of the present disclosure. FIG. 5a to 5c are schematic diagrams of deflection states of a deflection electrode assembly according to the embodiments of the present disclosure. FIGS. 4 and 5a to 5c schematically show one cathode unit 5, a part of the anode 6, a pair of adjacent tooth portions 12 and 22 of the deflection electrode assembly, and the electron beam passageway between the pair of adjacent tooth portions 12 and 22. It should be noted that in order to facilitate the explanation and prevent blurring of key points, the connecting portions of the electrode plates 1 and 2 and other components of the X-ray source are not shown in FIGS. 4 and 5a to 5c.

Below, the working principle of the X-ray source and deflection electrode assembly is described by taking the emission process of the electron beam (E1 as shown in FIG. 3) by one cathode unit 5 as an example. When cathode unit C1 of the plurality of cathode units 5 emits the electron beam E1, the electron beam E1 enters the corresponding electron beam passageway of the deflection electrode assembly at a certain initial speed (upward as shown in FIG. 3), specifically the electron beam passageway between tooth portion A1 of the tooth portions 12 of the electrode plate 1 and tooth portion B1 of the tooth portions 22 of the electrode plate 2. The potential controller 3 of the deflection electrode assembly controls the potential difference ($V_A$–$V_B$) between the electrode plate 1 and the electrode plate 2, such that the potential difference between the tooth portion 12 and the tooth portion 22 is in one of three states: $V_A$>$V_B$, $V_A$=$V_B$, and $V_A$<$V_B$. When the electron beam E1 moves between the tooth portion 12 (A1) and the tooth portion 22 (B1), it will deflect to A1 (to the left in FIG. 3), not deflect or deflect to B1 (to the right in FIG. 3) according to the potential difference between the tooth portion 12 and the tooth portion 22. As a result, the deflection electrode assembly produces a deflection effect on the electron beam. Further, when the electron beam E1 reaches the outlet position (the upper portion as shown in FIG. 3) of the electron beam passageway between the tooth portion 12 and the tooth portion 22, the cross-section area of the electron beam will decrease due to the focusing (as described in detail below). Therefore, the deflection electrode assembly and the X-ray source can further produce the focusing effect on the electron beam. After leaving the electron beam passageway, the electron beam E1 is accelerated by the high-voltage accelerating electric field between the anode 6 and the cathode unit 5 and hits the anode 6, thereby generating the X-rays. According to the embodiments of the present disclosure, the X-ray source can strengthen the focusing effect, thereby omitting the compensation electrode and further simplifying the structure; meanwhile, the two functions of focusing and deflection are designed on one integrated structure, thereby achieving the structural optimization of entirety.

FIG. 4 shows the focusing effect of the deflection electrode assembly according to some embodiments of the present disclosure. In the X-ray tube, the high voltage, usually tens to hundreds of kilovolts, is applied to the anode 6. The electrode plate 1 and electrode plate 2 of the deflection electrode assembly are located between the cathode 6 and the anode unit 5, and the potential difference between the electrode plate 1 and electrode plate 2 is far lower than the potential difference between the anode 6 and the cathode unit 5, usually not more than 3 kV, for example, within the range of plus or minus a few hundred volts. Therefore, a high-voltage accelerating electric field is formed between the anode 6 and the electrode plates 1 and 2 of the deflection electrode assembly. In an exemplary embodiment, as described above, the plane on which the upper surfaces of the tooth portions of the electrode plates 1 and 2 lie, is parallel to the electron beam receiving surface of the anode 6. In this case, the high-voltage accelerating electric field between the electron beam receiving surface of the anode 6 and the upper surfaces of the tooth portions of the electrode plates 1 and 2 is uniform in most areas, that is, the electric force lines are parallel, and the electric force lines of the high-voltage accelerating electric field are directed from the anode 6 to the upper surfaces of the tooth portions of the electrode plates 1 and 2.

However, since near the upper surfaces of the tooth portions of the electrode plates 1 and 2, there are electron beam passageways (gaps) between the tooth portions of the electrode plates 1 and the tooth portions of the electrode plate 2, the upper surfaces of the electrode plates 1 and 2 are not formed as a complete plane. A portion of the electric force lines of the high-voltage accelerating electric field enter the electron beam passageway and bend to point to the side surface of the tooth portion of the electrode plate 1 and/or the side surface of the tooth portion of the electrode plate 2, as shown in FIG. 4. Therefore, the electric force lines of the high-voltage accelerating electric field produce local deformation at the outlet position of the electron beam passageway. The electrons at the outlet position of the electron beam passageway move against the electric force lines in the high-voltage accelerated electric field, the electron beam will converge and focus at the outlet position of the electron beam passageway, and thus the cross-sectional area of the electron beam is reduced. In the X-ray source, such focusing effect is conducive to reducing the cross-sectional area of the electron beam, thereby reducing the size of the X-ray focus spot when the electron beam hits the anode, and the smaller the X-ray focus spot, the better the image quality of X-ray imaging.

FIGS. 5a to 5c show the deflection effect of the deflection electrode assembly according to the embodiments of the present disclosure. The deflection principle of the deflection electrode assembly is described below with three different potential difference states between the electrode plates 1 and 2 as examples. The potential controller (not shown in FIGS. 5a to 5c) controls to apply different potentials to the electrode plates 1 and 2 of the deflection electrode assembly, so that the potential difference ($V_A-V_B$) between the electrode plates 1 and 2 is one of the three states $V_A>V_B$, $V_A=V_B$, and $V_A<V_B$, and different electric field states are generated between the tooth portion 12 and the tooth portion 22.

In FIG. 5a, the potential difference between the electrode plates 1 and 2 is positive ($V_A>V_B$), which generates a deflection electric field between the tooth portion 12 and the tooth portion 22. In the deflection electric field between the tooth portion 12 and the tooth portion 22, the electric force lines are directed from the tooth portion 12 to the tooth portion 22. After the electron beam emitted by the cathode unit 5 enters the electron beam passageway between the tooth portion 12 and the tooth portion 22 at a certain initial speed, it will be subjected to the lateral force of the deflection electric field (against the direction of the electric force lines) and laterally deviate towards the tooth portion 12. As the electron beam will deflect towards the tooth portion 12 when passing through the electron beam passageway, the electron beam will hit the anode 6 at a position T1 corresponding to the tooth portion 12 and having a certain deviation, when it finally reaches the anode 6, and the X-rays will be generated at this position T1.

In FIG. 5b, the potential difference between the tooth portion 12 and the tooth portion 22 is zero ($V_A=V_B$), and there is no deflection electric field between the tooth portion 12 and the tooth portion 22. When the electron beam emitted by the cathode unit 5 enters the electron beam passageway between the tooth portion 12 and the tooth portion 22 at a certain initial speed, it will not be subjected to the lateral force of the deflection electric field, but will maintain to move in the original direction. Since the electron beam does not deflect when passing through the electron beam passageway, the electron beam will hit the anode 6 at a position T corresponding to a middle position between the tooth portion 12 and the tooth portion 22 when it finally reaches the anode 6, and the X-rays will be generated at this position T.

In FIG. 5c, the potential difference between the tooth portion 12 and the tooth portion 22 is positive ($V_A<V_B$), which generates a deflection electric field between the tooth portion 12 and the tooth portion 22. In the deflection electric field between the tooth portion 12 and the tooth portion 22, the electric force lines are directed from the tooth portion 22 to the tooth portion 12. After the electron beam emitted by the cathode unit 5 enters the electron beam passageway between the tooth portion 12 and the tooth portion 22 at a certain initial speed, it will be subjected to the lateral force of the electric field (against the direction of the electric force lines) and laterally deviate towards the tooth portion 22. As the electron beam will deflect towards the tooth portion 22 when passing through the electron beam passageway, the electron beam will hit the anode 6 at a position T2 corresponding to the tooth portion 22 and having a certain deviation, when it finally reaches the anode 6, and the X-rays will be generated at this position T2.

As can be seen, when there is a non-zero potential difference between the tooth portion 12 and the tooth portion 22, a deflection electric field is generated between the tooth portion 12 and the tooth portion 22. Due to the effect of the deflection electric field between the tooth portion 12 and the tooth portion 22, the electron beam will deflect when passing through the electron beam passageway, causing the deviation of the position where the electron beam hits the anode 6. The deviation amount of the position may relate to the initial speed of the electron beam, the absolute value of the potential difference ($V_A$-$V_B$) between the electrode plate 1 and electrode plate 2, the length of the electron beam passageway, etc. Generally, the greater the absolute value of the potential difference ($V_A$-$V_B$) between the electrode plate 1 and the electrode plate 2, the greater the deviation amount of the position.

Figure 6:
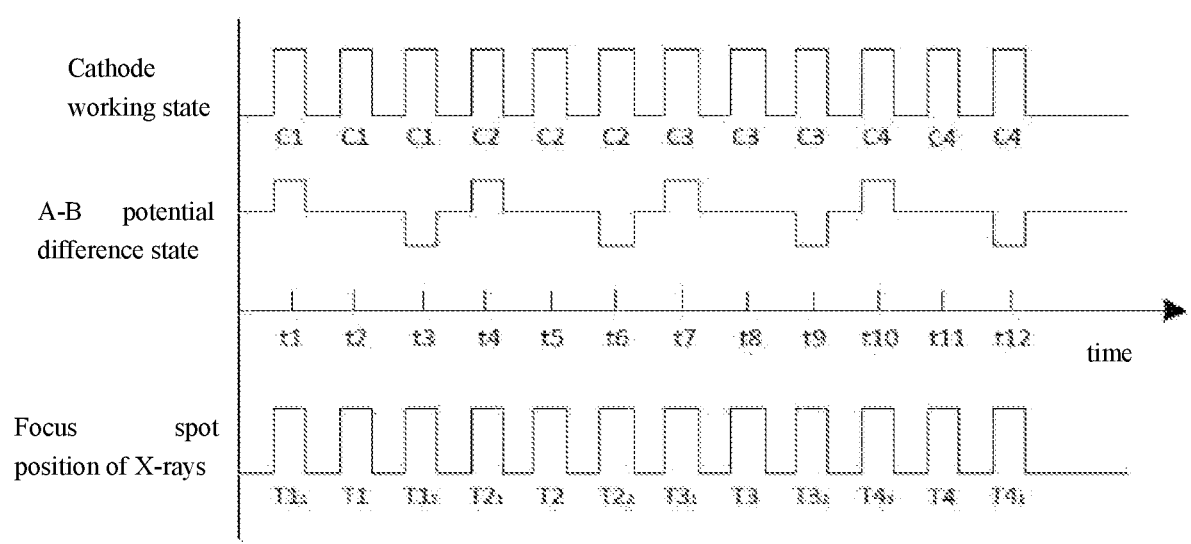
FIG. 6 is a timing chart of an operating state of an X-ray source according to an embodiment of the present disclosure.
Figure 7:
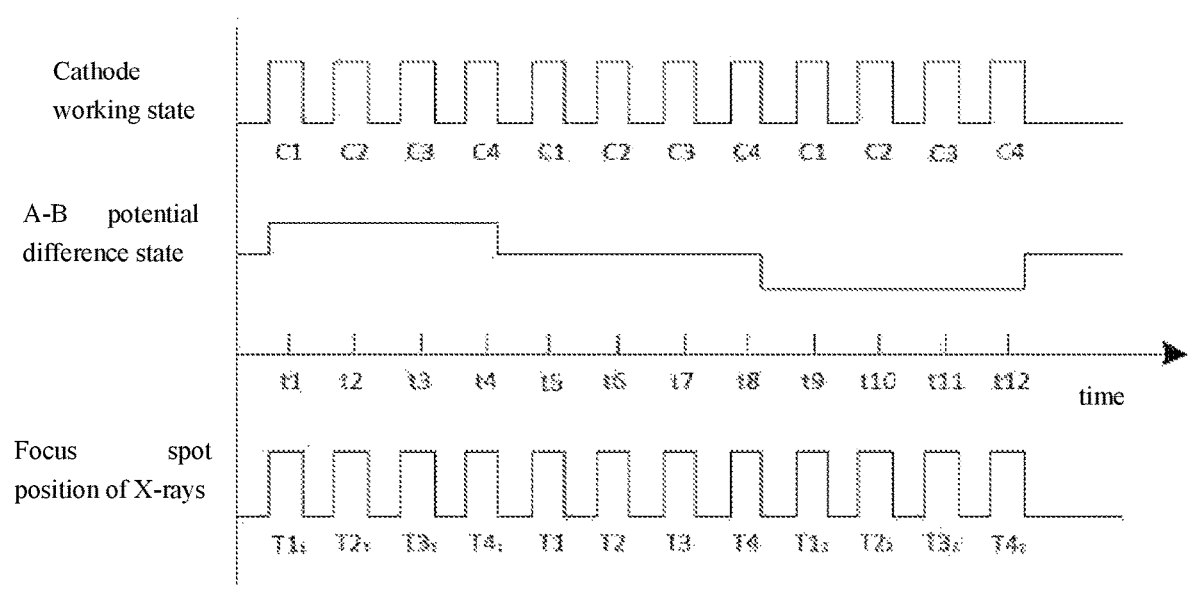
FIG. 7 is a timing chart of another operating state of an X-ray source according to an embodiment of the present disclosure.

Below, the operating state timing of the X-ray source according to some embodiments of the present disclosure is described with reference to FIGS. 6 and 7. FIG. 6 is a timing chart of an operating state of an X-ray source according to an embodiment of the present disclosure. FIG. 7 is a timing chart of another operating state of an X-ray source according to the embodiment of the present disclosure.

FIG. 6 shows an operating mode of an X-ray source including the deflection electrode assembly. The first line in FIG. 6 represents the electron beam emission state of a plurality of cathode units. The square wave of the first line includes two states: high and low, the high state represents generation of the electron beam, and C1, C2, C3, C4 . . . represent different cathode units that generate the electron beams. The second line represents the change state of the potential difference between the two electrode plates of the deflection electrode assembly. FIG. 6 illustrates three different potential difference states ($V_A$>$V_B$, $V_A$=$V_B$, and $V_A$<$V_B$) between the two electrode plates as examples. The square wave of the second line includes high, medium and low states, respectively representing three different potential difference states. The third line represents time, t1, t2, t3, t4 . . . are different times, and each time corresponds to generation of the electron beam once. The fourth line represents the change state of the electron beam receiving position on the anode, where T1, T2, T3, T4 . . . , represent the receiving position ranges corresponding to different cathode units, and the subscript represents the deviation state of position; meanwhile, the square wave of the fourth line includes high and low states, and the high state represents generation of the X-rays.

The electron beam receiving position (X-ray focus spot position) of the anode depends on the electron beam emission state of the cathode unit and the change state of the potential difference between the two electrode plates. In the embodiment shown in FIG. 6, at each time t1, t2, t3, t4 . . . , only one cathode unit is used to emit the electron beam, and at the same time, the potential difference ($V_A$-$V_B$) between the two electrode plates is in a definite state ($V_A$>$V_B$, $V_A$=$V_B$, or $V_A$<$V_B$).

In the embodiment shown in FIG. 6, the operating mode of the X-ray source is as follows: at equally spaced times t1, t2, t3, t4 . . . , each cathode unit emits electron beams for three times (C1 emits at the time t1, t2, t3, C2 emits at the time t4, t5, t6, and so on); for the three electron beam emissions of the same cathode unit, the deflection electrode assembly is respectively in three potential difference states (the potential difference is positive at the time t1, the potential difference is zero at the time t2, the potential difference is negative at the time t3, and so on). Thus, the electron beam receiving position changes successively on the anode. In some embodiments, the cooperative controller can record the corresponding electron beam receiving positions.

In such operating mode, the focus spot position (electron beam receiving position) of the X-ray source moves in sequence. For example, at the time t1, the cathode unit C1 generates the electron beam, $V_A$-$V_B$ is positive, and the focus spot position is T1$_1$; at the time t2, the cathode unit C1 generates the electron beam, $V_A$-$V_B$ is zero, and the focus spot position is T1; at the time t3, the cathode unit C1 generates the electron beam, $V_A$-$V_B$ is negative, and the focus spot position is T1$_2$; at the time t4, the cathode unit C2 generates the electron beam, $V_A$-$V_B$ is positive, and the focus spot position is T2$_1$; at the time t5, the cathode unit C2 generates the electron beam, $V_A$-$V_B$ is zero, and the focus spot position is T2; at the time t6, the cathode unit C2 generates the electron beam, $V_A$-$V_B$ is negative, and the focus spot position is T2$_2$; and so on. In this way, after all the cathode units have completed three successive electron beam emissions, the X-ray source can return to the initial state (time t1) for cyclic operation.

FIG. 7 shows another operating mode of the X-ray source including the deflection electrode assembly. The first line in FIG. 7 represents the electron beam emission state of a plurality of cathode units. The square wave of the first line includes two states: high and low, and the high state indicates generation of the electron beam. FIG. 7 illustrates four cathode units as examples, and C1, C2, C3 and C4 represent different cathode units that generate electron beams. The second line represents the change state of the potential difference between the two electrode plates of the deflection electrode assembly. FIG. 7 illustrates three different potential difference states ($V_A$>$V_B$, $V_A$=$V_B$, and $V_A$<$V_B$) between the two electrode plates as examples. The square wave of the second line includes high, medium and low states, respectively representing three different potential difference states. The third line represents time, t1, t2, t3, t4 . . . are different times, and each time corresponds to generation of electron beam once. The fourth line represents the change state of the electron beam receiving position on the anode, where T1, T2, T3 and T4 represent the receiving position ranges corresponding to different cathode units, and the subscript represents the deviation state of position; meanwhile, the square wave of the fourth line includes high and low states, and the high state represents generation of the X-rays.

The electron beam receiving position (X-ray focus spot position) of the anode depends on the electron beam emission state of the cathode unit and the change state of the potential difference between the two electrode plates. In the embodiment shown in FIG. 7, the same as in FIG. 6, at each time t1, t2, t3, t4 . . . , only one cathode unit is used to emit electron beam, and at the same time, the potential difference ($V_A$-$V_B$) between the two electrode plates is in a definite state ($V_A$>$V_B$, $V_A$=$V_B$, or $V_A$<$V_B$).

In the embodiment shown in FIG. 7, the operating mode of the X-ray source is as follows: at equally spaced times t1, t2, t3, t4 . . . , each cathode unit emits the electron beam once (C1 emits at the time t1, C2 emits at the time t2, C3 emits at the time t3, and so on); on the first emission cycle of the plurality of cathode units, the deflection electrode assembly remains in the first state of the three potential difference states; in the second emission cycle of the plurality of cathode units, the deflection electrode assembly remains in the second state of the three potential difference states; and in the third emission cycle of the plurality of cathode units, the deflection electrode assembly remains in the third state of the three potential difference states (for example, the potential difference is positive from the time t1 to the time t4, the potential difference is zero from the time t5 to the time t8, the potential difference is negative from the time t9 to the time t12, and so on). Thus, the electron beam receiving position changes successively on the anode. In some embodiments, the cooperative controller can record the corresponding electron beam receiving positions.

In such operating mode, the focus spot position of the X-ray source jumps. For example, taking an X-ray source with four cathode units as an example to describe, at the time t1, the cathode unit C1 generates the electron beam, $V_A-V_B$ is positive, and the focus spot position is $T1_1$; at the time t2, the cathode unit C2 generates the electron beam, $V_A-V_B$ is positive, and the focus spot position is $T2_1$; at the time t3, the cathode unit C3 generates the electron beam, $V_A-V_B$ is positive, and the focus spot position is $T3_1$; at the time t4, the cathode unit C4 generates the electron beam, $V_A-V_B$ is positive, and the focus spot position is $T4_1$; at the time t5, the cathode unit C1 generates the electron beam, $V_A-V_B$ is zero, and the focus spot position is T1; . . . ; at the time t8, the cathode unit C4 generates the electron beam, $V_A-V_B$ is zero, and the focus spot position is T4; at the time t9, the cathode unit C1 generates the electron beam, $V_A-V_B$ is negative, and the focus spot position is $T1_2$; . . . ; at the time t12, the cathode unit C4 generates the electron beam, $V_A-V_B$ is negative, and the focus spot position is $T4_2$. In this way, until all the cathodes emit electron beam for several times (for example, three times, and the number of times by which each cathode emits the electron beam, is the same as the number of potential difference states between the two electrode plates), the X-ray source can return to the initial state (time t1) and operate in cycle.

The working principle of the deflection electrode assembly and X-ray source have been described by taking three different potential difference states between the two electrode plates as examples. However, the present disclosure is not limited to this. According to the embodiments of the present disclosure, there may be two or more than four different potential difference states between the two electrode plates of the deflection electrode assembly.

Two electron beam emission states of the cathode unit have been described above. However, the present disclosure is not limited to this. According to the embodiments of the present disclosure, the cathode unit of the X-ray source can further have other electron beam emission states. In some embodiments, the electron beam emission states of the cathode unit can match the potential difference states between the two electrode plates. For example, when the number of potential difference states between the two electrode plates is n (n≥2), each cathode unit can emit electron beam for n times, or the plurality of cathode units can successively emit the electron beam once.

Two operating modes of the X-ray source are described above. However, the present disclosure is not limited to this. According to the embodiments of the present disclosure, the X-ray source can further have other operating modes. The operating mode of the X-ray source can achieve different distributions of the focus spot positions (electron beam receiving positions) of the X-ray source according to different combinations of the electron beam emission state of the cathode unit and the potential difference state between the two electrode plates.

As described above, only one cathode unit emits electron beam at the same time. However, the present disclosure is not limited to this. According to the embodiments of the present disclosure, the plurality of cathode units can emit electron beam at the same time.

According to some embodiments of the present disclosure, the operating mode of the X-ray source can be controlled by the cooperative controller 9. For example, the cooperative controller controls the electron beam emission of the cathode unit and the potential difference of the deflection electrode assembly according to the required focus spot position at each time). According to some embodiments of the present disclosure, the operating mode of the X-ray source can be controlled by other control devices, and the cooperative controller 9 can record the operating mode of the X-ray source (for example, including the emission time of the electron beam, the focus spot position, the X-ray generation time, the X-ray intensity, and the like).

As described above, the upper surfaces of the tooth portions of the electrode plates 1 and 2 lie in a plane parallel to the lower surface of the anode 6. However, the present disclosure is not limited to this. According to the embodiments of the present disclosure, the upper surface of the deflection electrode assembly (the upper surfaces of the tooth portions) may not be parallel to the lower surface of the anode 6.

As described above, the upper surfaces of the tooth portions of the electrode plates 1 and 2 are located in the same plane. However, the present disclosure is not limited to this. According to the embodiments of the present disclosure, the upper surfaces of the tooth portions of the electrode plates 1 and 2 may not be located in the same plane.

Figure 8:
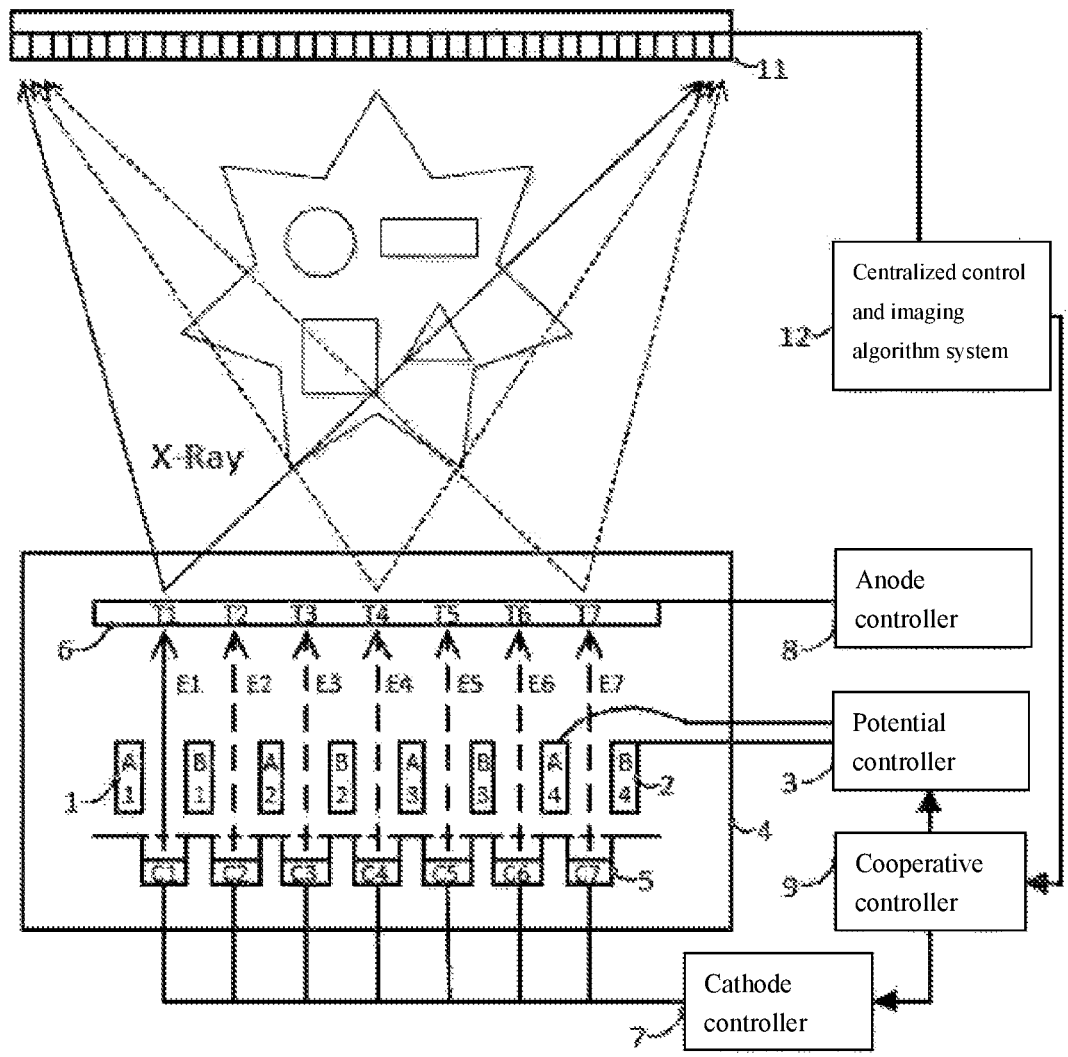
FIG. 8 is a schematic diagram of an X-ray imaging system according to an embodiment of the present disclosure.

Next, an X-ray imaging system according to the embodiments of the present disclosure will be described with reference to FIG. 8. FIG. 8 is a schematic diagram of an X-ray imaging system according to an embodiment of the present disclosure.

As shown in FIG. 8, the X-ray imaging system according to the embodiments of the present disclosure includes the X-ray source as described above and a detector 11. The description of the X-ray source according to the embodiments of the present disclosure please refer to above, and will not be repeated here. The X-ray source can generate X-rays from multiple positions (focus spot positions). The X-ray source according to the embodiments of the present disclosure can also be called a distributed X-ray source. The X-ray source is disposed opposite to the detector 11, so that an object under inspection can be located between the X-ray source and the detector 11. During the operation of the X-ray imaging system, the X-rays generated from the X-ray source can penetrate the object under inspection (such as luggage, industrial products, vehicles, special equipment, human body parts). The detector 11 is used to collect X-rays penetrating the object under inspection to generate X-ray acquisition information. According to some embodiments of the present disclosure, the detector 11 may include a plurality of detector units to form a detector array, or the detector 11 may be a flat panel detector. The present disclosure does not limit the layout of the X-ray source and the detector 11, as long as the X-rays emitted from the X-ray source can be collected by the detector 11 after penetrating the object under inspection. For example, the X-ray source and the detector 11 can be respectively arranged on two sides of the object under inspection, or can be arranged to completely or partially surround the object under inspection.

In an exemplary embodiment, the X-ray imaging system may further include an imaging control device 12. The imaging control device 12 can be connected with the X-ray source in communication, for example, is connected to the cooperative controller 9, the potential controller 3 and/or the cathode controller 7 of the X-ray source through wired communication or wireless communication. The imaging control device 12 can acquire the X-ray acquisition information from the detector 11 and the X-ray emission information from the X-ray source. For example, the imaging control device 12 can obtain the X-ray signals collected at different times from the detector 11, and obtain the information such as the X-ray emission position and intensity at the corresponding time from the X-ray source. The imaging control device 12 can generate an X-ray image (such as a two-dimensional image or a three-dimensional image) based on the X-ray acquisition information obtained from the detector 11 and the X-ray emission information obtained from the X-ray source. For example, the imaging control device 12 can construct an image (CT) reflecting the tomographic structure or three-dimensional information of the object under inspection through data analysis and processing and a reconstruction algorithm. In some embodiments, the imaging control device 12 may include a centralized control unit, a signal processing unit, a data conversion unit, an algorithm unit, an imaging display unit, and the like.

According to some embodiments of the present disclosure, the X-ray imaging system operates in the following manner: the imaging control device 12 of the X-ray imaging system determines the X-ray emission requirements (such as focus spot position at each time, X-ray generation duration, and X-ray intensity) according to the imaging requirements; the control device 12 sends the X-ray emission requirements to the X-ray source (such as the cooperative controller 9); the X-ray source controls (for example, through the cooperative controller 9) the working state of the cathode units 5 and the deflection electrode assembly according to the X-ray emission requirements, so as to generate the X-ray emission meeting the requirements; and the imaging control device 12 acquires the X-ray acquisition information from the detector 11 and the X-ray emission information from the X-ray source to generate the X-ray image.

According to some embodiments of the present disclosure, the X-ray imaging system operates in the following manner: the cooperative controller 9 of the X-ray source controls the working states of the cathode units 5 and the deflection electrode assembly to generate X-ray emission; the cooperative controller 9 transmits the X-ray emission information (including, for example, the focus spot position at each time, the X-ray generation duration, and the X-ray intensity) to the imaging control device 12 of the X-ray imaging system; and the imaging control device 12 acquires the X-ray acquisition information from the detector 11, and generates the X-ray image based on the X-ray acquisition information and the X-ray emission information.

The X-ray imaging system according to the embodiments of the present disclosure uses the distributed X-ray source with the deflection electrode assembly, and thus the number of focus spots generating X-rays is multiplied. Therefore, the perspective information for perspective imaging provided by the X-ray imaging system is multiplied and more refined perspective segmentation is provided, so that the quality of tomographic images or 3D CT images is further improved and high-definition imaging can be achieved. Further, the X-ray imaging system can provide clearer detection information (such as defect information) of the object under inspection, and thus has stronger automatic recognition capability.

Although the present disclosure has been described with reference to exemplary embodiments, it should be understood that the present disclosure is not limited to the construction and methods of the above embodiments. On the contrary, the present disclosure is intended to cover various modifications and equivalent configurations. In addition, although various elements and method steps of the disclosure are shown in various exemplary combinations and configurations, other combinations including more and fewer elements or methods fall within the scope of the present disclosure.

What is claimed is:

1. A deflection electrode assembly for an X-ray source, the deflection electrode assembly comprising:

a first electrode plate, comprising a first connecting portion and a plurality of first tooth portions, the plurality of first tooth portions being disposed on the first connecting portion and spaced apart from each other, and each first tooth portion extending from the first connecting portion so that the first electrode plate is formed into a comb shape;

a second electrode plate, comprising a second connecting portion and a plurality of second tooth portions, the plurality of second tooth portions being disposed on the second connecting portion and spaced apart from each other, and each second tooth portion extending from the second connecting portion so that the second electrode plate is formed into a comb shape, wherein the first electrode plate and the second electrode plate are arranged such that the first electrode plate and the second electrode plate do not contact each other, and that the plurality of first tooth portions and the plurality of second tooth portions are at least partially staggered to form a plurality of electron beam passageways, each electron beam passageway is located between adjacent first tooth portion and second tooth portion; and a potential controller electrically connected to the first electrode plate and the second electrode plate respectively, wherein the potential controller can supply electric power to the first electrode plate and the second electrode plate to generate a plurality of potential differences between the first electrode plate and the second electrode plate;

wherein the first electrode plate and the second electrode plate are arranged such that one second tooth portion is disposed between every two first tooth portions, and one first tooth portion is disposed between every two second tooth portions.

2. The deflection electrode assembly according to claim 1, wherein at each electron beam passageway, opposite side surfaces of adjacent first tooth portion and second tooth portion are parallel to each other.

3. The deflection electrode assembly according to claim 2, wherein the plurality of first tooth portions are spaced at the same spacing on the first connecting portion, the plurality of second tooth portions are spaced at the same spacing on the second connecting portion, and the plurality of electron beam passageways are distributed at the same spacing.

4. The deflection electrode assembly according to claim 3, wherein the plurality of first tooth portions have the same shape, and the plurality of second tooth portions have the same shape.

5. The deflection electrode assembly according to claim 4, wherein the first connecting portion comprises a first inner surface arranged with the plurality of first tooth portions, and the second connecting portion comprises a second inner surface arranged with the plurality of second tooth portions, the first inner surface is perpendicular to the side surfaces of the first tooth portions, and the second inner surface is perpendicular to the side surfaces of the second tooth portions.

6. The deflection electrode assembly according to claim 5, wherein each electron beam passageway comprises an input side of electron beam and an output side of electron beam; each first tooth portion of the first electrode plate comprises an upper surface on the output side of the electron beam and a lower surface on the input side of the electron beam, and the upper surfaces of the plurality of first tooth portions are all located in the same plane; each second tooth portion of the second electrode plate comprises an upper surface on the output side of the electron beam and a lower surface on the input side of the electron beam, and the upper surfaces of the plurality of second tooth portions are all located in the same plane.

7. The deflection electrode assembly according to claim 6, wherein the first electrode plate and the second electrode plate are arranged such that the upper surfaces of the plurality of first tooth portions and the upper surfaces of the plurality of second tooth portions are located in the same plane.

8. The deflection electrode assembly according to claim 7, wherein the first electrode plate and the second electrode plate are arranged such that the lower surfaces of the plurality of first tooth portions and the lower surfaces of the plurality of second tooth portions are all located in the same plane.

9. The deflection electrode assembly according to claim 8, wherein the first tooth portion and the second tooth portion both have a rectangular shape.

10. The deflection electrode assembly according to claim 6, wherein the first tooth portion comprises an end surface away from the first connecting portion, and the second tooth portion comprises an end surface away from the second connecting portion; and the first electrode plate and the second electrode plate are arranged such that a distance between the end surface of the first tooth portion and the second inner surface of the second connecting portion is in a range from 0.1 mm to 10 mm, and a distance between the end surface of the second tooth portion and the first inner surface of the first connecting portion is in a range from 0.1 mm to 10 mm.

11. The deflection electrode assembly according to claim 10, wherein the first electrode plate and the second electrode plate are arranged such that the distance between the end surface of the first tooth portion and the second inner surface of the second connecting portion is in a range from 0.5 mm to 5 mm, and the distance between the end surface of the second tooth portion and the first inner surface of the first connecting portion is in a range from 0.5 mm to 5 mm.

12. The deflection electrode assembly according to claim 11, wherein the first electrode plate and the second electrode plate are arranged such that each electron beam passageway has a length between 3 mm and 50 mm from the input side of the electron beam to the output side of the electron beam.

13. An X-ray source, comprising:
a plurality of cathode units, for generating electron beams from different positions;
an anode, for receiving the electron beams from different positions; and
the deflection electrode assembly according to claim 1, the first electrode plate and the second electrode plate of the deflection electrode assembly being arranged between the plurality of cathode units and the anode,
wherein each cathode unit is arranged to align one electron beam passageway of the deflection electrode assembly, so that the electron beams generated by the plurality of cathode units can pass through the corresponding electron beam passageways respectively and reach the anode.

14. The X-ray source according to claim 13, further comprising a cathode controller, which is electrically connected to the plurality of cathode units respectively to control each cathode unit to generate or not to generate the electron beam.

15. The X-ray source according to claim 14, further comprising a cooperative controller, which is connected with the cathode controller and the potential controller of the deflection electrode assembly in communication, so as to send an X-ray emission request to the cathode controller and the deflection electrode assembly or receive X-ray emission information from the cathode controller and the deflection electrode assembly.

16. The X-ray source according to claim 15, wherein n kinds of potential differences between the first electrode plate and the second electrode plate of the deflection electrode assembly are provided, n≥2, and the X-ray source comprises either of the following operating states:
the plurality of cathode units sequentially emit electron beams for n times, and for the n times of electron beam emission of each cathode unit, the deflection electrode assembly is respectively at the n kinds of potential differences; and
the plurality of cathode units performs n cycles of electron beam emission, and in the first cycle, the plurality of cathode units successively emit the electron beam once while the deflection electrode assembly remains at a first potential difference, until in the nth cycle, the plurality of cathode units successively emit the electron beam once while the deflection electrode assembly remains at the nth potential difference.

17. The X-ray source according to claim 13, wherein the upper surfaces of the plurality of first tooth portions of the first electrode plate are located in the same plane as the upper surfaces of the plurality of second tooth portions of the second electrode plate, and are parallel to a surface of the anode facing the first electrode plate and the second electrode plate.

18. An X-ray imaging system, comprising: the X-ray source according to claim 13 for generating X-rays from different positions, and an imaging control device for acquiring X-ray emission information from the X-ray source.

* * * * *